United States Patent [19]

Fedeli et al.

[11] 4,216,293

[45] Aug. 5, 1980

[54] EXTRACTING PROTEASE-INHIBITOR FROM ANIMAL TISSUE CONTAINING SAME

[75] Inventors: Gianfranco Fedeli, Milan; Luigi De Ambrosi, Trino, both of Italy

[73] Assignee: Laboraton Derivati Organici, S.p.A., Milan, Italy

[21] Appl. No.: 916,536

[22] Filed: Jun. 19, 1978

Related U.S. Application Data

[63] Continuation-in-part of Ser. No. 512,481, Oct. 4, 1974, abandoned.

[30] Foreign Application Priority Data

Oct. 5, 1973 [CH] Switzerland ................. 14265/73

[51] Int. Cl.$^2$ .............................................. C07G 7/00
[52] U.S. Cl. ................................................... 435/268
[58] Field of Search ................. 195/4, 29, 65; 435/268

[56] References Cited

U.S. PATENT DOCUMENTS

3,451,996   6/1969   Sumyk et al. .

FOREIGN PATENT DOCUMENTS

377159   4/1973   U.S.S.R. .

OTHER PUBLICATIONS

Methods in Enzymology, vol. 19, pp. 848–850 (1971).
Chemical Abstracts, 1973, vol. 79, 51999W (Abstract of U.S.S.R. Inv. Certif. 377,159, Apr. 1973).

*Primary Examiner*—Lionel M. Shapiro
*Attorney, Agent, or Firm*—Cushman, Darby & Cushman

[57] ABSTRACT

Protease inhibitor is extracted from fresh or frozen organs of slaughtered animals by an enzymolysis operation which excludes any possibility of interference by azymic autolysis, the enzymolysis being stopped after a time not exceeding 4 hours, whereafter a lysate aqueous solution is obtained by filtration and a quaternary ammonium base is added to the lysate solution to precipitate insolubles, the filtrate being the fraction which contains the expected protease inhibitor.

12 Claims, No Drawings

EXTRACTING PROTEASE-INHIBITOR FROM ANIMAL TISSUE CONTAINING SAME

CROSS-REFERENCE TO RELATED APPLICATION

This application is a continuation-in-part of application Ser. No. 512,481 filed Oct. 4, 1974, now abandoned.

FIELD OF THE INVENTION

This invention relates to the extraction of protease-inhibitor from animal tissues which contain such inhibitor and, more particularly, the trypsin-kallikrein inhibitor. Such protease inhibitors have interesting therapeutical properties, so that their use is now widespread in the medical and clinical practice.

BACKGROUND OF THE INVENTION

The principal object of this invention is to provide an improved and simplified method for extracting protease-inhibitors from animal tissues which contain such inhibitors.

Another object of this invention is to provide a method for extracting protease inhibitors which contain a very reduced percentage of pyrogenic substances and polyanionic pollutants such as mucopolysaccharides and nucleic acids.

Still another object of the present invention is to provide a method for extracting protease inhibitors from animal tissues which contain such inhibitors without interfering with other methods directed towards the extraction of other useful substances, such as heparin, from animal tissues; it will be appreciated that the method of the present invention permits to extract heparin, if so desired, from an intermediate fraction which contains heparin, it being however understood that the method according to this invention is directed essentially and predominantly to the extraction of protease inhibitors.

According to the preferred embodiment of this invention, a method is suggested for extracting a protease-inhibitor from protease-inhibitor-containing fresh or frozen organs of slaughtered animals, said organs showing no signs of incipient or progressed azymic autolysis, said method comprising the steps of (a) comminuting said organs;

(b) subjecting said comminuted organs to enzymolysis by contacting them, within an aqueous medium, with at least one proteolytic enzyme selected from the group of the proteolytic enzymes which do not naturally occur in said organs and which are inactive towards said protease-inhibitor to be extracted;

(c) discontinuing said enzymolysis and collecting a lysate aqueous solution by subjecting the aqueous medium containing said comminuted organs and said at least one proteolytic enzyme to filtration;

(d) adding a quaternary ammonium base to said lysate aqueous solution to obtain the precipitation of an insoluble fraction;

(e) filtering off said insoluble fraction and collecting the inhibitor-containing filtrate, and (f) recovering said protease-inhibitor from said filtrate.

It is preferred that the proteolytic enzyme referred to above be a member selected from the group consisting of papain, ficin bromelin, Alkalase (R.T.M.) and Neutrase (R.T.M.).

The enzymolysis is stopped, at the proper instant of time, by any of the method as conventionally used for such an operation: heating to 90° C. and over is a preferred method, but other methods can be used, such as the addition of a deproteinating agent or otherwise, since it matters to stop the enzymolysis when desired, rather than the means used for the discontinuation.

The enzymolysis should be conducted under the optimum conditions for the proteolytic enzyme selected. If papain is used, a temperature of 60° C.±2° C. with a pH from 5.0 to 6.0 are preferred conditions, and a pH of 5.5 is an optimum. If ficin is the selected proteolytic enzyme, the conditions preferred for papain apply again. If bromelin is used, a lower temperature, such as 37° C.±2° C. is preferred, the preferential pH being near 6.

If the proteolytic enzyme used is Alkalase (R.T.M.) the optimum temperature is 65° C.±2° C., the pH is preferred to be near 7.2 and the enzymolysis time does not exceed 150 mins. When using Neutrase (R.T.M.) the preferred temperature is 60° C.±2° C., the preferred pH in the neighbourhood of 6.7 and the time, again, does not exceed 150 mins. for the enzymolysis step.

According to the invention, the preferred quaternary ammonium bases are cetylipiridinium and cetyltrimethylammonium bromide.

Other features, properties and advantages of the invention will become apparent as the present description proceeds.

ABRIDGED REVIEW OF THE PRIOR ART

B. Kassel and coworkers, J.Biol.Chem. 219, 203, and H. Kraut and coworkers, Z.physiol.Chem., 334, 236. disclose that protease-inhibitors are not chemically attacked by several proteolytic enzymes; among these, pepsin, trypsin, chymotrypsin, kallikrein, plasmin, elastase, collagenase, A- and B-carboxypeptidase, ficin, papain and bromelin are listed. It is thus an acquired knowledge that papain, ficin and bromelin are not affected by the protease inhibitor and this is the reason why they are used in the present invention, the more so that the quantity of the inhibitor contained in the animal organs concerned is very small as compared with the quantity of enzyme which is employed.

Summing up, these references disclose the properties of the protease inhibitors and define them, but afford no teaching as to the use of enzymes for extracting such inhibitors.

On the basis of these prior teachings, it was reasonably unpredictable that enzymes which do not affect the protease inhibitor might indicate the first step of an efficient procedure for extracting the inhibitor from organs which contain it.

An exhaustive listing of proteolytic enzymes can be found in B. Kassel, Method of Enzymology, Vol. 19, pages 848–850.

The U.S. Pat. No. 3,451,996 to G. B. Sumyk et al, of June 24, 1969 discloses a method for the preparation of heparin and adopts what is called an "autolysis" step: from the perusal of this reference it would seem that by "autolysis" both an azymic and an enzymic lysis are indifferently intended. In the present specification, the term "autolysis" will never be used to indicate "enzymolysis, since it may be conducive to language confusion. By "autolysis", the present specification and the claims appended thereto, shall intend a process of azymic decomposition, either incipient or progressed, which is quite assimilable to a putrefaction or meat-ripening process, and animal tissues under such autolytic conditions shall never be used for this invention. In this invention, it is no question at all of adding, or not, "additional enzymes to the tissue because the enzymes present will complete the digestion process" as indicated by Sumyk on Col. 2, lines 11-13. Additionally, it is added that Sumyk works under definitely alkaline conditions with a pH of 6.5 to 8 for extracting heparin. Moreover, in the present invention, there is no digestion process to be completed, either.

An indication of "autolysis" in the proper acception can be found in the USSR Pat. No. 377.159 to L. B. Polonskaya et al, of Apr. 17, 1973: a "meat-ripening" process proper, which lasts as long as 17 hours is adopted. In this connection, be it understood that the present invention must, compulsorily and of necessity, be performed under such conditions as to exclude in an absolute and total manner, each and every phenomenon of "autolysis" of the animal organ tissue itself and the method of the invention must be carried out under the optimum conditions of the enzyme concerned, as specified above and specifically claimed hereinafter. As a matter of fact, the autolysis proper as suggested in the USSR patent above mentioned is conducive, with certainty, to the formation of histamine and pyretogens, does not permit that limpid filtrates may be obtained and the operations specified therein cannot be performed on an industrial scale, i.e. on large amounts of animal tissues. Upon autolysis, there is in the USSR patent cited above, a 2-hour step of centrifugation and washing: the experience of the present applicant has shown that 13 hours of centrifugation and washing are actually necessary.

Last, but not least, the method according to this invention, as will be seen, takes no more than 4 hours for the "enzymolysis" so that, in addition to being comparatively simple and inexpensive, it is also quick. Comparison test data will be given hereinafter, which fully support these views.

Other references, which may be of some interest are:
M. Kunitz and J. H. Northrop, J. Gen. Physiol. 19, 991
Werle E. and coworkers—Z. Naturforsch. 14b, 385
Astrup, T. Acta Physiol. Scand. 26, 243
German Patents: 1 084 433-1 148 352-1 011 576-956 907-950 959 and 954 284
British Patent 965 352
French Patent 1 566 777
Japanese Patents: 43-7328 and 44-8563.

DESCRIPTION OF THE PREFERRED EMBODIMENTS

In order that the invention may be better understood, together with the best mode to carry it out into constructive practice, the ensuing examples will be given.

EXAMPLE 1

Ten (10) kilograms of ground beef lung have been slurried in 16 liters of distilled water. Upon gentle heating of the mass to 40° C. there has been added, with stirring, a suspension of 20 grams of papain in 4 liters of a 0.25 M buffer citrate at a pH of 5.5, containing 200 grams of magnesium sulphate. The temperature has been adjusted to 60° C. and the mass has been maintained in these conditions during 4 hours. Then the pH has been adjusted to 6.2 by increments of concentrated ammonia and the mass has been heated to 90° C. Subsequently, the whole has been filtered under pressure and the residue has been discarded. The clear liquid has been treated with cetylpiridinium until a complete flocculation of the polyanions has been obtained. Filtration has then been effected in order to collect the heparin-containing precipitate, while the liquid has been supplemented with trichloroacetic acid up to a final concentration of 3%. After 30 minutes pressure filtration has been carried out again while effecting the washing on the filter with 4 liters of 3% trichloroacetic acid. Thus, there have been obtained 32 liters of a clear liquid having an activity of 610 inhibiting I.U. per cubic centimeter (I.U.=inhibitor unit, see Z. Physiol.Chem. 182, 1–1930) equivalent to a yield of $1.95 \times 10^6$ I.U. per kg of starting organ. This solution has then been subjected to fractionation with ammonium sulphate between 0.5 and 0.9 of saturation by collecting the precipitate by centrifuging. At this state there have been obtained 85 grams of precipitate containing $1.9 \times 10^7$ I.U. (about 98% of the total activity as obtained in the lysis) whereas the contents of proteinic material was 36.5%, that which indicates a purity of 1.56 micrograms per I.U. The further purifications carried out with the methods which are conventional in the art have permitted to obtain 465 cubic centimeters of an apyrogenic solution having an activity as high as 32,000 I.U. per cubic centimeter, that is, a total of $1.49 \times 10^7$ I.U., a fact which indicates a yield of 76% as compared with the initial activity. The purity, as found in the analysis of the proteinic material, was 0.143 micrograms per I.U.

A comparative test on a corresponding portion of the same organ, in the ground state, by extraction with 70% ethanol in the presence of calcium chloride (see German Pat. No. 1 084 433) has given a yield of $0.875 \times 10^6$ I.U. per kilogram of organ at the level of raw product and $0.322 \times 10^6$ I.U. per kilogram of organ, with a purity of 0.14 micrograms per I.U. at a purified level. These data, compared with those obtained by the papainic lysis correspond to yields of 21.7% at a purified product level and of 46% at the level of raw product. Another test, still made on a corresponding amount of the same organ, but ground, applying the method as disclosed by B. Kassell in "Methods Enzymology" Vol. 19, page 845, has given a yield, in raw product, of $1.020 \times 10^6$ I.U. per kilogram of organ and of $0.418 \times 10^6$ I.U. per kilogram of organ at the level of a purified organ. These data, compared with those obtained by papainic lysis correspond to yields of 53.6% at raw product level and of 28% at the purified product level.

EXAMPLE 2

The same procedure as in example 1 has been adopted by replacing papain by ficin. The yields have been $2.03 \times 10^6$ I.U. per kilogram of lung at raw product level and $1.64 \times 10^6$ I.U. per kilogram of lung at purified product level.

EXAMPLE 3

Five (5) kilograms of ground beef lung have been slurried in 8 liters of water and there have been added 2 liters of a suspension containing 10 grams of bromelin in a phosphate buffer (0.1 M) at a pH of 6 containing 1% of ethylene diamino tetra acetic acid. The mass has been gently heated to 37° C. and under these conditions it has been maintained during 4 hours. At the end of this time, the temperature has been raised to 90° C. during 10 minutes. Subsequently, the mass has been filtered under pressure by washing on the filter with 2 liters of distilled water. The filtrate, upon cooling, has been treated with cetyltrimethylammonium bromide until complete flocculation of the polyanions has been achieved, the latter being collected on a filter in order to separate heparin. The clear filtrate has given 16 liters with an activity of 540 I.U. per cubic centimeter, that which corresponds to a yield of $1.735 \times 10^6$ I.U. per kilogram of starting organ. Purification has then been proceeded with as disclosed in example 1. The final yield of the purified product has been $1.18 \times 10^6$ I.U. per kilogram of lung. A comparison test carried out by extraction and fractionation with ammonium sulphate, as disclosed in the French Pat. No. 1 566 777, has given a final yield of purified product of $6.8 \times 10^6$ I.U. per kilogram of starting organ, that which corresponds to 57.7% of the yield as obtained with the method as described in this example.

EXAMPLE 4

2.5 kilograms of powdered dry beef lung have been extracted according to the outline of example 1. The final yield has been 3.2 by $10^6$ I.U. per kilogram of powdered dry beef lung.

The following examples 5 and 6 show that the method of this invention can equally well be applied to two other enzymes now available on the market, i.e. Alkalase and Neutrase (Reg.Trade Marks).

EXAMPLE 5

5 kilograms of ground beef lung are slurried in 8 liters of water and the slurry is supplemented with two liters of a suspension containing 10 grams of Alkalase (Reg.-Trade Mark of Novo Industrie A.S. of Bagsvaerd, Denmark) in a 0.1 molar, pH 7.2 triethanolamine buffer. On completion of this addition, the reaction mixture is heated to 65° C.±2° C. for 2 hours 30 mins. to effect the enzymolysis. On completion of this step, the procedure is the same as in Example 1 hereinabove. The yield is $1.8 \cdot 10^6$ I.U. per kilogram of raw material.

EXAMPLE 6

It is conducted under the very same conditions as in Example 6 above, the only exceptions being that the pH in the enzymolysis step is 6.7 and the temperature is 60° C.±2° C. The yield is $1.9 \cdot 10^6$ I.U.

The enzymolysis according to this invention is significant in that it does away, at the very outset, with the proteins which might block the protease-inhibitor in the final purification stages: matter-of-factly, by carrying out the enzymolysis as directed herein, proteins of the kind referred to just now are no longer present as such, but in the form of aminoacids and peptides, and these latter do not block the protease inhibitor at all.

In addition, to have removed the noxious proteins referred to above is a fact which drastically reduces any hazard of occurrence of anaphylactic shocks due to proteinaceous pollutants.

Two comparative test runs have been carried out, in order to compare the teachings of the present invention with the teachings of the prior art disclosures as represented by U.S. Pat. No. 3,451,996 to Sumyk et al, and the USSR Pat. No. 377 159 to Polonskaya et al. It is to be observed that the comparison with Sumyk et al has been made in spite of the fact that the teachings of Sumyk et al are prevailingly directed to the production of heparin.

COMPARISON TEST RUN 1

The test run has been made on 1 kilogram of bovine lung tissue having a homogeneous texture.

| Test data | SUMYK | POLON-SKAYA | APPLI-CANT |
|---|---|---|---|
| Enzymic lysis time, hrs | 48 | — | 3 |
| Azymic autolysis time, hrs | | 17 | |
| Bacteriostasis | required (xylene) | not indicated | unnecessary |
| Filtration or centrifugation time, hours | 1 | 6 | 1 |
| Type of filtrate | limpid | turbid | limpid |
| K.I.U. per kg, activity | 130.000±5% | 480.000±5% | 440.000±5% |
| Degree of enzymic lysis | 0.56 | — | 0.46 |
| Degree of azymic autolysis | | 0.16 | |

The "degree of lysis" in its general acceptance is the ratio of the aminic nitrogen to the total nitrogen: here, the distinction between enzymic lysis and azymic autolysis has been expressly made, consistently with the considerations which have been made in the foregoing. At any rate, the above test run shows, without any doubt, that in three hours only of enzymolysis, the present method gives higher yields both in terms of kallikrein-inhibiting activity (K.I. Units) and in terms of the other parameters tabulated above.

COMPARISON TEST RUN 2

The tests have been repeated under different conditions and the results are individually tabulated below.

| Method of Polonskaya et al | | |
|---|---|---|
| Azymic autolysis time, hrs | 3 | 17 |
| Filtration or centrifugation time, hrs | 14 | 13 |
| K.I.U. after filtration, per kg | 431.000 | 480.000 |
| K.I.U. after final purification, per kg | 109.000 | 100.000 |
| Method of Sumyk et al | (pancreas) | (papain) |
| Enzymolysis time, hrs | 48 | 24 |
| Filtration or centrifugation time, hrs | 1 | 1 |
| K.I.U. after filtration, per kg | 190.000 | 90.000 |
| K.I.U. after final purification, per kg | 180.000 | 10.000 |
| Applicant's method | | |
| Enzymolysis time, hrs | 1.5 | 3 |
| Filtration time, hrs | 1 | 1 |
| K.I.U. after filtration, per kg | 280.000 | 440.000 |
| K.I.U. after final purification, per kg | 190.000 | 280.000 |

The above tabulated results confirm, once again, both the rapidity and the versatility of the method of this invention.

We claim:

1. A method for extracting a protease-inhibitor from protease-inhibitor-containing fresh or frozen organs of slaughtered animals, said organs showing no signs of incipient or progressed azymic autolysis, said method comprising the steps of:
   (a) Comminuting said organs;
   (b) and before said organs show signs of incipient or progressed anzymic autolysis subjecting said comminuted organs to enzymolysis by contacting them, within an aqueous medium, with at least one proteolytic enzyme selected from the group if the proteolytic enzymes which do not naturally occur in said organs and which are inactive towards said protease-inhibitor to be extracted;
   (c) Discontinuing said enzymolysis and collecting a lysate aqueous solution by subjecting the aqueous medium containing said comminuted organs and said at least one proteolytic enzyme to filtration;

(d) Adding a quaternary ammonium base to said lysate aqueous solution to obtain the precipitation of an insoluble fraction;

(e) Filtering off said insoluble fraction and collecting the inhibitor-containing filtrate, and (f) Recovering said protease-inhibitor from said filtrate.

2. Method according to claim 1, wherein said at least one proteolytic enzyme is a member selected from the group consisting of papain, ficin, bromelin, Alkalase (T.M.) and Neutrase (T.M.).

3. Method according to claim 1, wherein said inhibitor is recovered from said inhibitor-containing filtrate by acidifying said filtrate with 2% to 5% of trichloroacetic acid and subsequently fractionating said acidified filtrate by adding thereto ammonium sulphate to a concentration thereof of between 45% and 90% of the concentration corresponding to the saturation at room temperature.

4. Method according to claim 1, wherein said bovine animal organs are bovine lungs.

5. Method according to claim 1, wherein said enzymolysis is conducted using papain as the proteolytic enzyme, at a temperature of 60° C.±2° C., a pH of from 5.0 to 6.0 and for a time not exceeding 4 hours.

6. Method according to claim 1, wherein said enzymolysis is conducted using bromelin as the proteolytic enzyme, at a temperature of 37° C.±2° C., a pH of 6 and for a time not exceeding 4 hours.

7. Method according to claim 1, wherein said enzymolysis is conducted using ficin as the proteolytic enzyme, at a temperature of 60° C.±2° C., a pH of from 5.0 to 6.0 and for a time not exceeding 4 hours.

8. Method according to claim 1, wherein said enzymolysis is conducted using Alkalase (R.T.M.) as the proteolytic enzyme, at a temperature of 65° C.±2° C., a pH of 7.2 and for a time not exceeding 150 minutes.

9. Method according to claim 1, wherein said enzymolysis is conducted using Neutrase (R.T.M.) as the proteolytic enzyme, at a temperature of 60° C.±2° C., a pH of 6.7 and for a time not exceeding 150 minutes.

10. Method according to claim 1, wherein the enzymolysis is discontinued by heating the aqueous medium containing said comminuted organs and said at least one proteolytic enzyme to a temperature of 90° C. and over.

11. Method according to claim 1, wherein said quaternary ammonium base is selected from the group consisting of cetylpiridinium and cetyltrimethylammonium bromide.

12. Method according to claim 1, wherein said protease inhibitor is trypsin-kallikrein inhibitor.

* * * * *